(12) United States Patent
Azegami et al.

(10) Patent No.: US 10,292,685 B2
(45) Date of Patent: May 21, 2019

(54) ULTRASONIC DIAGNOSTIC APPARATUS

(71) Applicant: Toshiba Medical Systems Corporation, Otawara-shi (JP)

(72) Inventors: Mio Azegami, Nasushiobara (JP); Chihiro Shibata, Nasushiobara (JP); Takuya Sasaki, Nasu (JP); Shigemitsu Nakaya, Nasushiobara (JP); Masao Takimoto, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 394 days.

(21) Appl. No.: 14/955,822

(22) Filed: Dec. 1, 2015

(65) Prior Publication Data
US 2016/0081667 A1 Mar. 24, 2016

Related U.S. Application Data

(63) Continuation of application No. PCT/JP2014/066207, filed on Jun. 18, 2014.

(30) Foreign Application Priority Data

Jun. 19, 2013 (JP) .................................. 2013-128514

(51) Int. Cl.
*A61B 8/00* (2006.01)
*G01S 7/52* (2006.01)
(Continued)

(52) U.S. Cl.
CPC .................. *A61B 8/54* (2013.01); *A61B 8/14* (2013.01); *G01S 7/52053* (2013.01);
(Continued)

(58) Field of Classification Search
CPC ... G01S 7/52053; G01S 7/52098; A61B 8/54; A61B 8/14; A61B 8/465; A61B 8/5207; A61B 8/464; A61B 8/467
See application file for complete search history.

(56) References Cited

U.S. PATENT DOCUMENTS

| | | | | |
|---|---|---|---|---|
| 6,450,979 B1 * | 9/2002 | Miwa | ................. | A61H 23/0245 600/439 |
| 2009/0099482 A1 * | 4/2009 | Furuhata | ................. | A61N 7/00 601/2 |
| 2010/0016719 A1 * | 1/2010 | Freiburger | ............... | A61B 8/00 600/443 |

FOREIGN PATENT DOCUMENTS

| JP | 4-156832 A | 5/1992 |
|---|---|---|
| JP | 2004-305347 | 11/2004 |

(Continued)

OTHER PUBLICATIONS

Vivid User Manual, GE Medical Systems, Operating Documentation, Copyright © 2005 by General Electric Co.*

(Continued)

*Primary Examiner* — Bo Joseph Peng
(74) *Attorney, Agent, or Firm* — Oblon, McClelland, Maier & Neustadt, L.L.P.

(57) ABSTRACT

An ultrasonic diagnostic apparatus according to an embodiment acquires a tomogram of a subject and displays the tomogram, based on a reception signal which is obtained by transmitting/receiving ultrasonic waves to/from the subject. The apparatus comprises maximum value memory circuitry, select circuitry, and an ultrasonic output controller. The maximum value memory circuitry stores a maximum value of an index value relating to an ultrasonic output, with respect to each of scan regions of the subject. The ultrasonic output controller acquires, from the maximum value memory circuitry, the maximum value of the index value (Continued)

corresponding to the scan region selected by the select circuitry, and controls the ultrasonic output such that the ultrasonic output does not exceed the maximum value of the index value.

10 Claims, 5 Drawing Sheets

(51) Int. Cl.
*A61B 8/14* (2006.01)
*A61B 8/08* (2006.01)

(52) U.S. Cl.
CPC .......... *G01S 7/52098* (2013.01); *A61B 8/464* (2013.01); *A61B 8/465* (2013.01); *A61B 8/467* (2013.01); *A61B 8/5207* (2013.01)

(56) References Cited

FOREIGN PATENT DOCUMENTS

| | | |
|---|---|---|
| JP | 2005-241267 | 9/2005 |
| JP | 2006-95278 | 4/2006 |
| JP | 2010-259662 | 11/2010 |
| JP | 2011-19588 | 2/2011 |
| JP | 2011-87709 | 5/2011 |
| JP | 2011-120706 | 6/2011 |
| JP | 2012-205610 | 10/2012 |
| JP | 2013-55978 | 3/2013 |

OTHER PUBLICATIONS

Vivid Reference Manual, GE Medical System, Reference Documentation, Copyright © 2005 by General Electric Co.*
Medical Ultrasound Safety, Third Edition, Feb. 6, 2014.*
M7/M7T, Diagnostic Ultrasound System Operator's Manual, Nov. 2010 (Year: 2010).*
EdanUSA, User Manual, Aug. 2012 (Year: 2012).*
International Search Report dated Jul. 29, 2014 in PCT/JP2014/066207 filed Jun. 18, 2014 (with English Translation).
Written Opinion dated Jul. 29, 2015 in PCT/JP2014/066207 filed Jun. 18, 2014.
Office Action dated May 8, 2018 in Japanese Patent Application No. 2014-125698.

* cited by examiner

ULTRASONIC DIAGNOSTIC APPARATUS

CROSS-REFERENCE TO RELATED APPLICATIONS

This application is a Continuation Application of PCT application No. PCT/JP2014/066207, filed on Jun. 18, 2014, and is based upon and claims the benefit of priority from Japanese Patent Application No. 2013-128514, filed on Jun. 19, 2013, the entire contents of which are incorporated herein by reference.

FIELD

Embodiments described herein relate generally to an ultrasonic diagnostic apparatus.

BACKGROUND

An ultrasonic diagnostic apparatus is an apparatus which radiates ultrasonic pulses, which are generated from an ultrasonic transducer built into an ultrasonic probe, into a subject, receives reflected waves from a subject tissue or bloodstream by the ultrasonic transducer, and generates and displays image data, etc.

In this ultrasonic diagnostic apparatus, examples of index values, which are indicative of the effects of ultrasonic waves on a living body, include an MI (mechanical index) value, a TI (thermal index) value, and an Ispta (spatial-peak temporal-average intensity) value.

The MI value is an index value for evaluating the safety of a nonthermal action (mechanical action) of ultrasonic waves on a living body, and is defined as a value obtained by dividing a negative peak sound pressure by a square root of a central frequency. By the MI value, it is possible to express a generation process of cavitation which affects a living body tissue, such as a process in which a gas dissolved in a body fluid becomes bubbles due to a variation in pressure caused by ultrasonic waves.

The TI value is an index value for evaluating the safety of a thermal action of ultrasonic waves on a living body, and expresses the intensity of an ultrasonic output by a ratio thereof to an output of ultrasonic waves that is set at 1, by which the temperature of a living body tissue is raised by one degree by absorption attenuation of ultrasonic waves.

The Ispta value is a temporal average value of sound intensity at a point at which the sound intensity takes a maximum value in a sound field, and is defined as an intensity value of an ultrasonic output at a time when a value (pulse-intensity integral (PII)), which is obtained by time-integrating an instantaneous intensity of ultrasonic pulses, is averaged by a pulse-repetition period.

The recommendable maximum values of these index values are indicated by guidelines. Incidentally, the contents of the guidelines vary from country to country. For example, in the U.K., since a nonthermal action by ultrasonic waves is large in the scan of a fetus, eye and skull, a lower MI value is indicated as a recommendable maximum value (recommendable maximum MI value) for this scan than in the scan of other diagnosis regions. In addition, in the case of the U.K., in consideration of a thermal action by ultrasonic waves, a recommendable maximum scan time is indicated for each TI value. However, only for the purpose of research or only when necessary, is an examination permitted under the condition that a greater biological effect than under the recommended condition may be caused, with the responsibility being taken by the operator.

In some cases, the above-described index values relating to the ultrasonic output increase unintentionally due to a change of parameters such as a focus, a frequency, etc. during an examination.

Thus, in the ultrasonic diagnostic apparatus, there is a function for controlling the ultrasonic output so as to maintain a preset target MI value, even when parameters have been changed. In general, this function is used in a contrast-enhanced examination mode, in order to suppress the rupture of bubbles due to the effect of the mechanical action of ultrasonic waves. In addition, there is a function which makes it possible to select whether an ultrasonic output is to be controlled so as to maintain a preset target MI value or an ultrasonic output is to be controlled so as to maintain a target ultrasonic output, in accordance with the kind of diagnosis, for example, according to whether special diagnosis using a contrast medium is performed or not.

In the conventional ultrasonic diagnostic apparatus, there is no particular problem in usual cases. However, according to the inventor's study, there is room for improvement in that there is no function for setting maximum values of index values relating to ultrasonic outputs for individual scan regions such as a fetus, eye and skull.

Supplementarily, in the conventional ultrasonic diagnostic apparatus, there is room for improvement in that there is no function for suppressing the biological effect of ultrasonic waves to maximum values or less of index values for individual regions, and for maintaining safety, regardless of scan mode, such as a contrast-enhanced examination mode and other modes.

It is an object to provide an ultrasonic diagnostic apparatus which can suppress the biological effect of ultrasonic waves to the maximum value or less of the index value for each scan region, and can maintain safety, regardless of scan mode.

DETAILED DESCRIPTION

In general, according to one embodiment, an ultrasonic diagnostic apparatus according to an embodiment is configured to acquire a tomogram of a subject and to display the tomogram, based on a reception signal which is obtained by transmitting/receiving ultrasonic waves to/from the subject.

The ultrasonic diagnostic apparatus includes maximum value memory circuitry, select circuitry and an ultrasonic output controller.

The maximum value memory circuitry stores a maximum value of an index value relating to an ultrasonic output, with respect to each of scan regions of the subject.

The select circuitry is capable of arbitrarily selecting a scan region of the subject.

The ultrasonic output controller acquires, from the maximum value memory circuitry, the maximum value of the index value corresponding to the scan region selected by the select circuitry, and controls the ultrasonic output such that the ultrasonic output does not exceed the maximum value of the index value.

Ultrasonic diagnostic apparatuses according to embodiments will be described hereinafter with reference to the accompanying drawings. In each of the embodiments, the case is described in which an MI value is used as an index value relating to an ultrasonic output. However, the index value is not limited to the MI value, and an arbitrary index value, such as a TI value or an Ispta value, is similarly applicable. Here, the term "ultrasonic output" may be read as "acoustic output" or "acoustic power". In addition, in the second and following embodiments, structural elements, which are substantially identical to the structural elements in a preceding embodiment, are denoted by like reference numerals, and a description thereof is omitted. Structural elements, which are different from those in the preceding embodiment, will mainly be described.

<First Embodiment>

Figure 1:
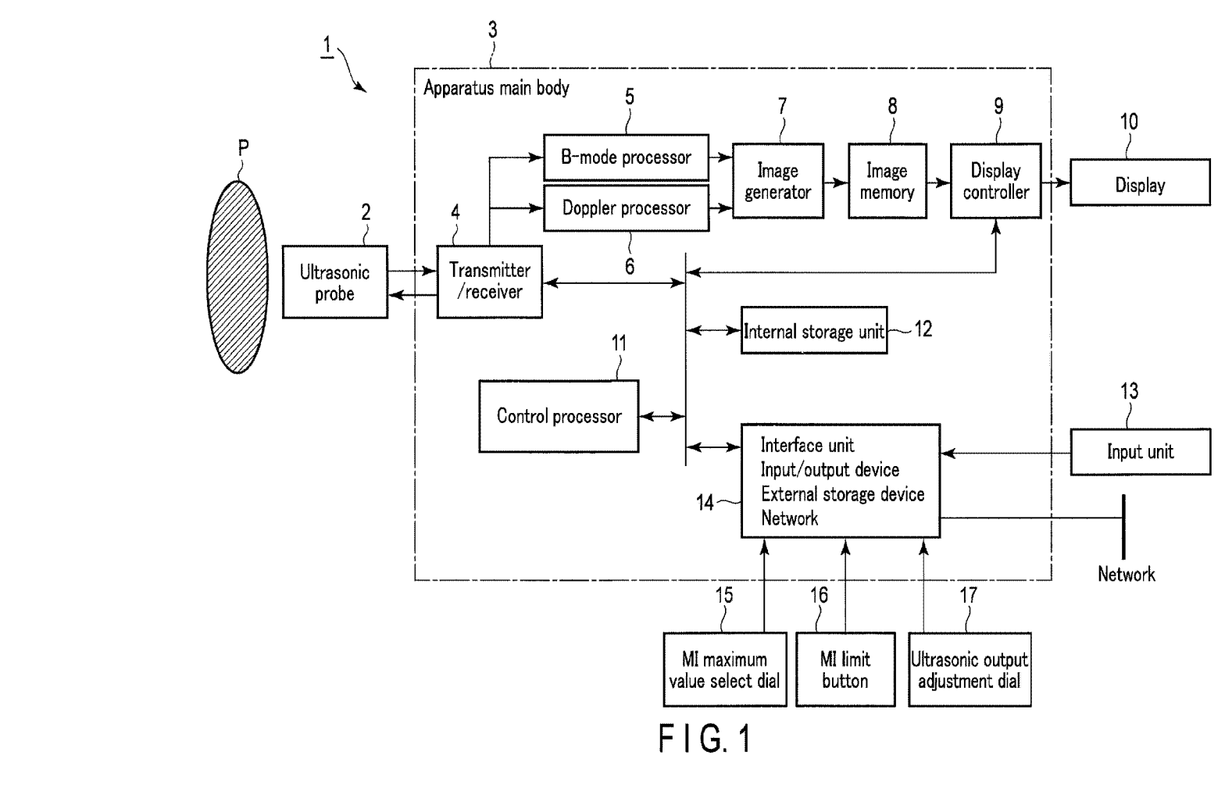
FIG. 1 is a schematic view illustrating the configuration of an ultrasonic diagnostic apparatus according to a first embodiment.

FIG. 1 is a block diagram illustrating the configuration of an ultrasonic diagnostic apparatus according to a first embodiment. An ultrasonic diagnostic apparatus 1 includes an ultrasonic probe 2, an apparatus main body 3, a transmitter/receiver 4, a B-mode processor 5, a Doppler processor 6, an image generator 7, an image memory 8, a display controller 9, a display 10, a control processor 11, an internal storage unit 12, an input unit 13, an interface unit 14, an MI maximum value select dial 15, an MI limit button 16, and an ultrasonic output adjustment dial 17.

The ultrasonic probe 2 generates ultrasonic waves, based on a driving signal from the transmitter/receiver 4, and converts reflected waves from a subject to an electric signal.

If ultrasonic wave is transmitted from the ultrasonic probe 2 to a subject P, the transmitted ultrasonic wave is successively reflected by discontinuous planes of acoustic impedance of a body tissue, and is received by the ultrasonic probe 2 as an echo signal.

In addition, an echo, in a case in which transmitted ultrasonic pulses are reflected by a surface of a moving bloodstream, a heart wall, etc., undergoes a frequency shift by the Doppler effect, depending on a velocity component in an ultrasonic transmission direction of the moving body.

The transmitter/receiver 4 includes a pulse generator, a delay circuit and a pulser as a transmission system. In the pulser, a rate pulse for forming transmission ultrasonic waves is repeatedly generated at a predetermined rate frequency fr [Hz] (period; 1/fr second). In the delay circuit, a necessary delay time for converging ultrasonic waves in a beam shape for each channel and for determining transmission directivity is given to each rate pulse. The pulse generator applies driving pulses to the ultrasonic probe 2 at a timing based on this rate pulse.

In addition, the transmitter/receiver 4 includes a preamplifier, an A/D converter, a reception delay unit and an adder as a reception system. The preamplifier amplifies, with respect to each channel, an echo signal (reception signal) which was received via the ultrasonic probe 2. The reception delay unit imparts a necessary delay time for determining a reception directivity of the amplified echo signal. The adder adds echo signals to which the delay time was imparted. By the addition, a reflected component from a direction corresponding to the reception directivity of echo signals is emphasized, and a comprehensive beam of ultrasonic transmission/reception is formed by the reception directivity and transmission directivity.

The B-mode processor 5 includes a wave detector and a logarithmic compressor. The wave detector receives an echo signal from the transmitter/receiver 4, and executes an envelope detection process. The logarithmic compressor executes logarithmic amplification of the echo signal after the wave detection in the above wave detection process, and generates data in which the signal intensity is expressed by the degree of luminance.

The Doppler processor 6 frequency-analyzes velocity information from the echo signal received from the transmitter/receiver 4, extracts blood-stream, tissue and contrast medium echo components by the Doppler effect, and obtains bloodstream information, such as an average velocity, dispersion and power, with respect to multiple points. The obtained bloodstream information undergoes a predetermined process in the image generator 7, etc., and is then color-displayed as a combination image with an average velocity image, a dispersion image and a power image.

The image generator 7 generates ultrasonic images such as a B-mode image and a CFM (color flow mapping) mode image, based on the data that is output from the B-mode processor 5 and Doppler processor 6. The generated ultrasonic images are output to the image memory 8.

The image memory 8 is composed of a storage memory which stores frame-by-frame ultrasonic images that were output from the image generator 7. The ultrasonic images can be read out, for example, after diagnosis, and can be reproduced as still images, or as a moving picture using a plurality of ultrasonic images.

The display controller 9 reads out the ultrasonic image from the image memory 8, generates a diagnosis screen in which the read-out image and character information, etc. are composited, and causes the display 10 to display the diagnostic image. In the meantime, when the ultrasonic probe 2 is driven in units of a predetermined time width, and ultrasonic transmission/reception is performed, the display controller 9 lays out, on the same screen, ultrasonic images (tomograms of the subject) of the same frame of respective mode images which are stored in the image memory 8, generates a diagnostic image in which the laid-out images and character information, etc. are composited, and causes the display 10 to display the diagnosis screen.

The display 10 is, for example, an LCD (liquid crystal display), and is controlled by the display controller 9 to display the above-described diagnosis screen, etc.

The input unit 13 includes various switches, buttons, a trackball, a mouse, a keyboard, etc. for taking into the apparatus main body 3 various instructions, conditions, a setup instruction of a region-of-interest (ROI), and various image quality condition setup instructions from the operator.

The interface unit 14 is an interface for connecting various input/output devices, a communication network, an external storage device, etc. to the apparatus main body 3. Data, such as ultrasonic images, analysis results, etc., which were obtained in the ultrasonic diagnostic apparatus 1, can be output via the interface unit 14 to the above-described input/output devices, other devices connected to the communication network, and the above-described external storage device.

The MI maximum value select dial 15 is configured to adjust, by the operator's operation, the maximum value of the MI value of each scan region, which is written in preset information in the internal storage unit 12.

The MI limit button 16 is configured to control the ON/OFF of an ultrasonic output control function by the control processor 11 by the operator's operation, and is displayed, for example, on a TCS (touch command screen) or the display 10. However, the MI limit button 16 may be provided as a hardware key. The ultrasonic output control function may be called an ultrasonic output suppression function.

The ultrasonic output adjustment dial 17 is configured to adjust the ultrasonic output by the operator's operation.

The internal storage unit 12 stores data such as various scan sequences and ultrasonic transmission conditions, a control program for causing the control processor 11 to realize various functions, system information, preset information, patient information, operator identification information, etc. For example, by a preset select screen G1 illustrated in FIG. 2, it is possible to selectively set the preset information with respect to each scan region such as the abdomen, a fetus (OB: obstetrics, fetal heart), or a skull (TCD). This preset information includes, in addition to ordinary preset information, a maximum value of an index value relating to an ultrasonic output with respect to each scan region of the subject.

The ordinary preset information includes values of condition items in the initial state of the apparatus operation, and the condition items include adjustment items which the operator can adjust. The adjustment items are items relating to an examination mode, a scan mode, a scan condition, a signal process condition, a display condition, etc.

Figure 3:
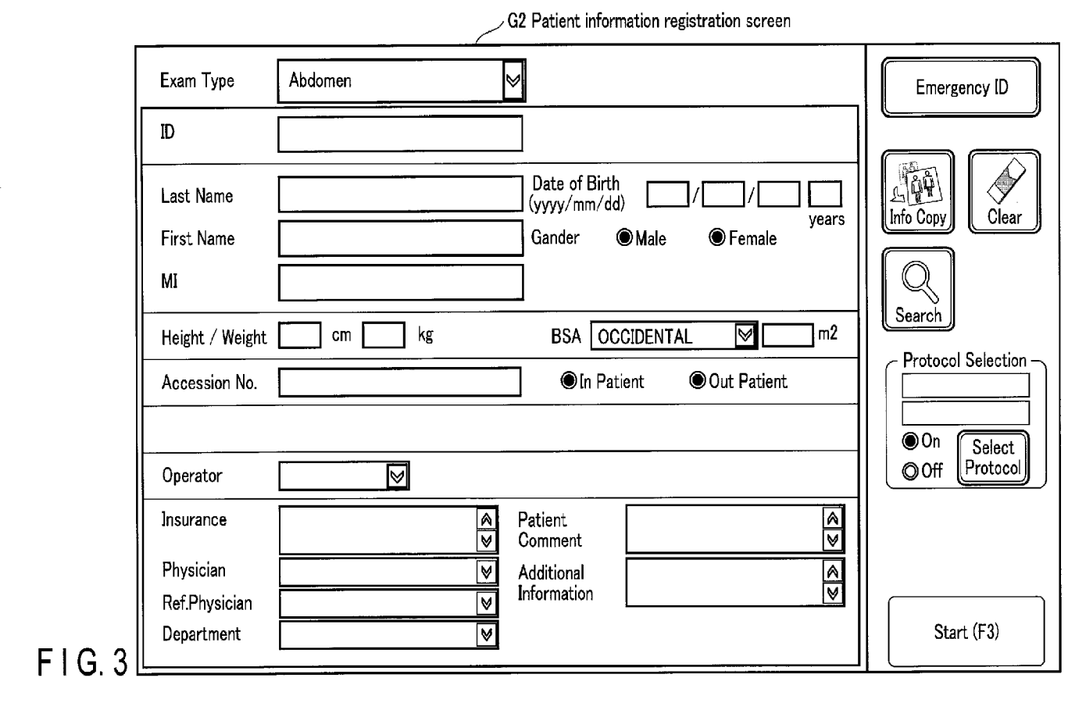
FIG. 3 is a schematic view illustrating an example of a patient information registration screen in the embodiment.

The patient information is, for example, information including items and values in a patient information registration screen G2 illustrated in FIG. 3, and includes patient identification information (name, ID, date of birth), a scan region ("Exam Type" in the Figure), etc.

As the operator identification information, for example, an operator ID and an operator name may be mentioned.

The control processor 11 controls the operations of the respective parts of the ultrasonic diagnostic apparatus 1. In addition, the control processor 11 executes the control program stored in the internal storage unit 12, thereby realizing a select function and an ultrasonic output control function. The select function is a function which can arbitrarily select a scan region of the subject, and can arbitrarily select, for example, a choice relating to a desired region of the subject. The ultrasonic output control function is a function which acquires, from the internal storage unit 12, the maximum value of the index value corresponding to the scan region selected by the select function, and controls the ultrasonic output based on the maximum value of the index value.

As the method of controlling the ultrasonic output, a method of increasing/decreasing a voltage or current applied to the ultrasonic probe 2 is possible, in addition to a method of changing transmission conditions such as a transmission frequency, a burst wave number, etc. The "voltage applied to the ultrasonic probe 2" may be called "transmission voltage" or "driving voltage". In the present specification, use is made of a method of changing the magnitude of the ultrasonic output by changing not the transmission condition but the transmission voltage.

Figure 4:
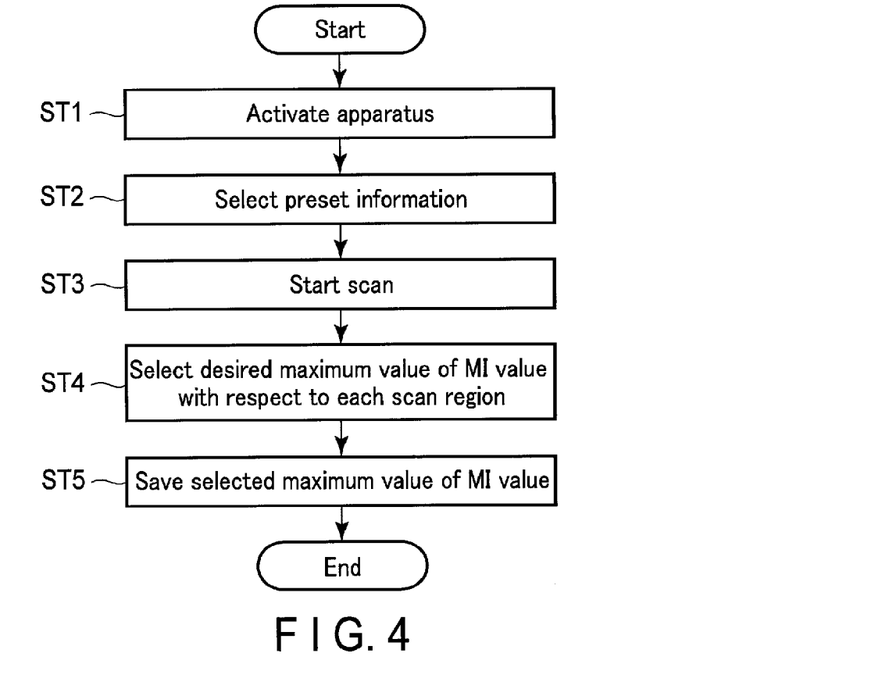
FIG. 4 is a flowchart for describing an operation in the embodiment.

Next, the operation of the ultrasonic diagnostic apparatus 1 with the above-described configuration is described with reference to a flowchart of FIG. 4.

Figure 2:
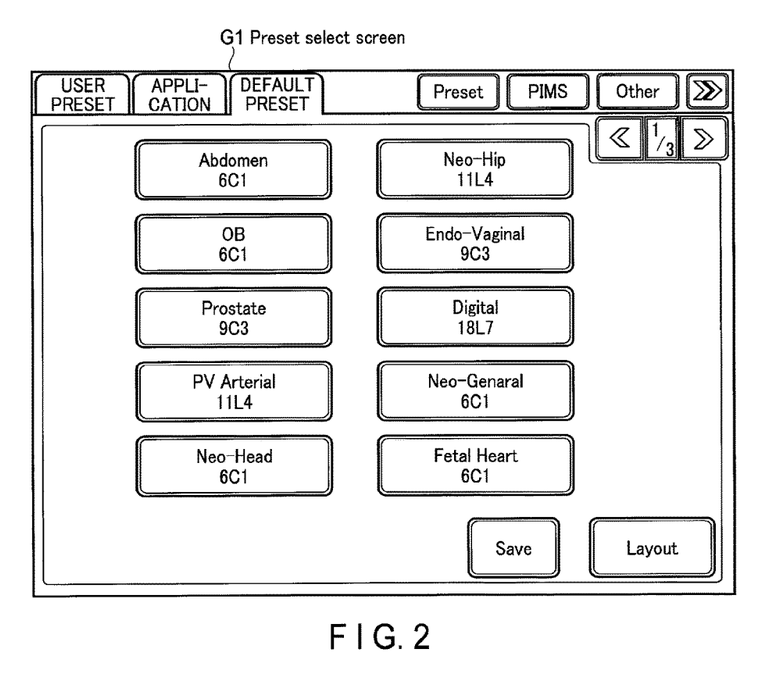
FIG. 2 is a schematic view illustrating an example of a preset select screen in the embodiment.

If the ultrasonic diagnostic apparatus 1 is activated by, for example, an operation of the input unit 13 by an operator (ST1), a patient ID is input by an operation of the input unit 13 by the operator. Based on the input patient ID, the control processor 11 searches the internal storage unit 12, and causes the display 10 to display the patient information registration screen G2, based on the obtained patient information. The operator recognizes a scan region "Abdomen" which is displayed on the patient information registration screen G2. On the preset select screen G1, preset information corresponding to the scan region can be selected from a plurality of pieces of preset information.

In the ultrasonic diagnostic apparatus 1, if a select button in the preset select screen G1 is touch-operated by the operator, the control processor 11 selects a scan region which is indicated by the select button. In addition, the control processor 11 selects preset information corresponding to the selected scan region (ST2), and reads out the preset information from the internal storage unit 12.

Next, the ultrasonic diagnostic apparatus 1 starts a scan by the operator's operation (ST3).

During the execution of the scan, a desired maximum value of an MI value is selected for each scan region by the operation of the MI maximum value select dial 15 (ST4). If a save button (not shown) is pressed, the control processor 11 saves the selected maximum value of the MI value in the preset information for each scan region (ST5). This preset information is updated and saved in the internal storage unit 12.

Subsequently, in the ultrasonic diagnostic apparatus 1, the ultrasonic probe 2 is driven to transmit/receive ultrasonic waves to/from a patient (subject), acquires a tomogram of the scan region of patient, based on the obtained reception signal, and displays the tomogram on the display 10.

At this time, the control processor 11 acquires from the internal storage unit 12 the maximum value of the MI value (the MI value saved in step ST5) which corresponds to the selected scan region, controls an ultrasonic output so as not to exceed the maximum value of the MI value, and executes a scan.

The above is the main operation flow in this embodiment.

In the present embodiment, with the use of the above-described apparatus configuration, a preset is created for each scan region of the subject. Thereby, the maximum value of the index value (e.g., MI value) relating to the ultrasonic output is stored. If the scan region is selected, the maximum value of the index value corresponding to the selected scan region is acquired, and the ultrasonic output is controlled so as not to exceed the maximum value of the index value. Accordingly, regardless of the scan mode, it is possible to suppress the biological effect due to ultrasonic waves down to the maximum value or less of the index value for each scan region, and to maintain safety. In the meantime, in step ST5, the maximum value of the MI value, which was selected in step ST4, may be saved in the preset information for each kind of ultrasonic probe. In addition, at a time of shipment from the maker, the maximum value of the index value relating to the ultrasonic output, which varies among countries for shipment, may be saved. Specifically, the maximum value of the MI value may be a value which is set based on the kind of ultrasonic probe, aside from the scan region, or may be a value which is set based on the country for shipment (the regulation value of the country for shipment) of the ultrasonic diagnostic apparatus. When the selected maximum value of the index value (e.g., MI value) is stored with respect to each scan region, each kind of ultrasonic probe, and each country for shipment, it becomes possible to safely perform an examination under the condition matching with the need of each operator by suppressing the biological effect due to ultrasonic waves down to the maximum value or less of the index value for each kind of ultrasonic probe and each country for shipment, in addition to the above-described advantageous effects.

In addition, the control processor 11 may control the ultrasonic output such that the ultrasonic output may not exceed the maximum value of the index value in all scan modes. Specifically, the maximum value of the index value may be made common among all sub-modes, and, after the preset information was once created, the maximum value of the index value may be applied to all scan methods (B-mode, color mode, pulse Doppler mode, etc.).

Next, a description is given of a method of selecting a maximum value above the maximum value of the MI value in the preset information, under the judgment of the operator, with respect to a case of executing a scan with an MI value exceeding the maximum value of the MI value in the preset information. For example, with respect to the maximum value of the index value relating to the ultrasonic output, when the standard of the country for clinical use differs from that for research use, or when a diagnosis target (e.g., fetus) is invisible with the maximum value stored in the preset information, it is possible to adapt to this by the following operation.

While a scan is being executed, a maximum value above the maximum value of the MI value in the preset information is selected by operating the MI maximum value select dial 15. However, the save button is not operated.

Thereby, with the operation of the ultrasonic output adjustment dial 17, the target region of the patient can be scanned with an ultrasonic output exceeding the maximum value of the MI value in the preset information. However, the ultrasonic output at this time is controlled by the control processor 11 so as not to exceed the maximum value that was selected by the operation of the maximum value select dial 15.

<Second Embodiment>

Next, referring to FIG. 1, an ultrasonic diagnostic apparatus according to a second embodiment is described.

The present embodiment is a modification of the first embodiment. The control processor 11 of the ultrasonic diagnostic apparatus 1 is configured to realize a first display function (f1), an adjustment function (f2), a first switching function (f3), and a write function (f4) by executing the control program.

(f1) A first display function which displays a current index value relating to an ultrasonic output on the display 10 via the display controller 9. The first display function, the display controller 9 and the display 10 constitute a first display. In the meantime, the first display function (f1) may be independently applied to each embodiment (even in a case where related functions (f2) to (f4) are not executed).

(f2) An adjustment function which adjusts an ultrasonic output in accordance with the operator's operation on the ultrasonic output adjustment dial 17, when the ultrasonic output control function is in an OFF state. The ultrasonic output adjustment dial 17 and the adjustment function (f2) constitute an adjuster. The adjuster is not limited to the ultrasonic output adjustment dial 17, and an arbitrary input interface is usable.

(f3) A first switching function which effects switching between an ON state and an OFF state of the ultrasonic output control function by the operator's operation on the MI limit button 16. The MI limit button 16 and the first switching function (f3) constitute first switching circuitry. The first switching circuitry is not limited to the MI limit button 16, and an arbitrary input interface is usable.

(f4) A write function which writes, if the ultrasonic output control function is switched to the ON state by the first switching function, the current index value, which is being displayed in accordance with the adjusted ultrasonic output, as the maximum value in the preset information (or system information) in the internal storage unit 12.

Here, the adjustment function (f2) and first switching function (f3) can change the maximum value in the internal storage unit 12 to the current index value via the write function (f4).

For example, with respect to the maximum value of the index value relating to the ultrasonic output, there is a case in which the standard of the country for clinical use differs from that for research use, or a case in which a diagnosis target of ultrasonic diagnosis is invisible with the current maximum value.

The ultrasonic diagnostic apparatus 1 can adapt to even these cases, by the configuration which changes the maximum value (relating to the ultrasonic output) in the internal storage unit 12 in accordance with the operation of the adjustment function (f2) and first switching function (f3).

In addition, the control processor 11 may realize the following functions (f5) to (f10) by executing the control program.

(f5) A comparison function which compares the current index value displayed on the display 10, and the maximum value (for each scan region) in the internal storage unit 12.

(f6) An alert function which outputs an alert to the operator, when the current index value is the maximum value or more as the result of the comparison. As the alert, color display, sound output, message display or a combination thereof may be used, as appropriate. For example, an alert may be output by display on the display 10, or an alert sound may be output from a buzzer (not shown), or a voice alert may be output from a speaker (not shown).

(f7) A second switching function which effects switching between an ON state and an OFF state of the alert function by the operator's operation on an alert ON/OFF button (not shown). The alert ON/OFF. button and second switching function (f7) constitute a second switching circuitry. The second switching circuitry is not limited to the alert ON/OFF button, and an arbitrary input interface is usable.

(f8) A second display function which displays, at a preset start time, a confirmation message which prompts confirmation of the maximum value (for each scan region) in the internal storage unit 12, on the display 10 via the display controller 9. The second display function, the display controller 9 and the display 10 constitute a second display.

(f9) A third switching function which effects switching between an ON state and an OFF state of the second display function by the operator's operation on a confirmation message ON/OFF button (not shown). The confirmation message ON/OFF button and the third switching function (f9) constitute third switching circuitry. The third switching circuitry is not limited to the confirmation message ON/OFF button, and an arbitrary input interface is usable.

(f10) A third display function which displays, on the display 10 via the display controller 9, whether the maximum value for each scan region in the internal storage unit 12 is the preset maximum value or less. Here, the "preset maximum value" may be read as "preset recommendable maximum value for each scan region".

However, the functions (f1) to (f10) are arbitrary additional matters, and may be omitted.

Figure 5:
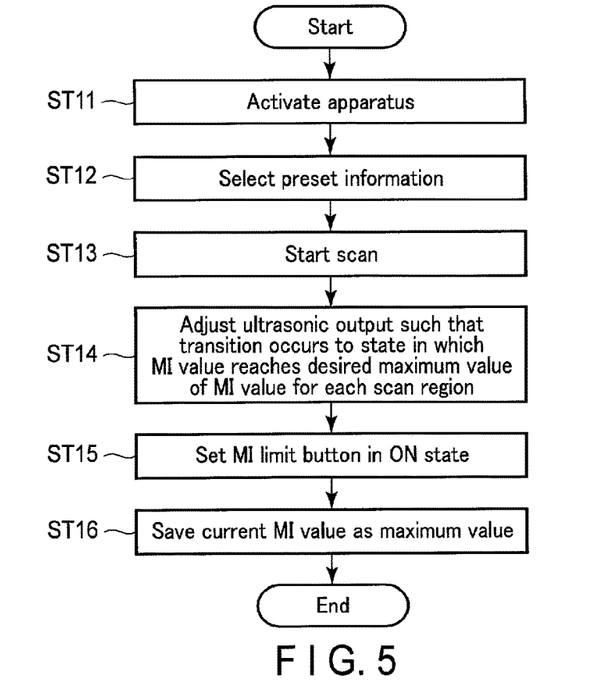
FIG. 5 is a flowchart for describing an operation of an ultrasonic diagnostic apparatus according to a second embodiment.

Next, the operation of the ultrasonic diagnostic apparatus with the above-described configuration is described with reference to a flowchart of FIG. 5.

To start with, like the above-described steps ST1 to ST3, the ultrasonic diagnostic apparatus 1 executes steps ST11 to ST13, and starts a scan. It is now assumed that, in the ultrasonic diagnostic apparatus 1, the ultrasonic control function of the control processor 11 is in the OFF state. In addition, it is assumed that, in the ultrasonic diagnostic apparatus 1, the control processor 11 displays the current MI value, which relates to the ultrasonic output, on the display 10 via the display controller 9.

In the ultrasonic diagnostic apparatus 1, the ultrasonic output is adjusted in accordance with the operator's operation on the ultrasonic output adjustment dial 17, and the ultrasonic output is lowered until the displayed MI value reaches the desired maximum value of the MI value with respect to each scan region (ST14). Thereby, the currently displayed MI value becomes the desired maximum value corresponding to the scan region.

In the ultrasonic diagnostic apparatus 1, the control processor 11 changes the OFF state of the ultrasonic output control function to the ON state, by the operator's operation on the MI limit button 16 (ST15).

In the ultrasonic diagnostic apparatus 1, if the ultrasonic output control function is switched to the ON state, the displayed current MI value is written as the maximum value in the preset information in the internal storage unit 12 in accordance with the adjusted ultrasonic output (ST16). In this manner, in the ultrasonic diagnostic apparatus 1, the maximum value of the MI value in the preset information, which is stored in the internal storage unit 12, can be changed to the current maximum value in accordance with the operator's operation.

Next, a description is given of a method of selecting a maximum value above the maximum value of the MI value in the preset information, in connection with a case of executing a scan with an MI value exceeding the maximum value of the MI value in the preset information under the judgment of the operator for a certain purpose, as described in the first embodiment.

While a scan is being executed, the control processor 11 changes the ON state of the ultrasonic output control function to the OFF state by the operator's operation on the MI limit button 16. In this state, by executing steps ST14 to ST16 once again, the maximum value above the maximum value of the MI value in the preset information can be selected, and the preset information can be changed to the selected maximum value.

As has been described above, according to the above-described embodiment, the current index value relating to the ultrasonic output is displayed. When the ultrasonic output control function is in the OFF state, the ultrasonic output is adjusted in accordance with the operator's operation, and the ON state and OFF state of the ultrasonic output control function are switched by the operator's operation. If the ultrasonic output control function is switched to the ON state, the displayed current index value is written as the maximum value in accordance with the adjusted ultrasonic output. Specifically, the adjustment function (f2) and first switching function (f3) of the control processor 11 change the maximum value of the index value in the internal storage unit 12 to the current index value via the write function (f4).

Therefore, according to the present embodiment, in addition to the advantageous effects of the first embodiment, the maximum value of the index value relating to the ultrasonic output can be changed to a desired value with respect to each scan region.

Additionally, according to the present embodiment, by the comparison function (f5) and alert function (f6), when the displayed current MI value and the maximum value of the MI value in the preset information are compared and an alert is output to the operator if the current MI value is this maximum value or more, it is possible to prevent a biological action with a high ultrasonic output from being erroneously applied to the patient during an examination. In addition, by the configuration in which the second switching function (f7) effects switching between the ON state and OFF state of the alert by the operator's operation, the alert can be stopped, where necessary, according to the use such as for research. Thus, the operator can be protected from such unnecessary alerts.

Additionally, according to the present embodiment, by the second display function (f8), when a confirmation message prompting confirmation of the maximum value of the index value for each scan region is displayed at a preset start time, it is possible to prevent a biological action with a high ultrasonic output from being erroneously applied to the patient during an examination. In addition, by the configuration in which the third switching function (f9) effects switching between the ON state and OFF state of the display of the confirmation message by the operator's operation, the operator can be protected from an unnecessary confirmation message, where necessary, where appropriate for research use, like the case described above.

Additionally, according to this embodiment, by the third display function (f10), when it is displayed that the maximum value of the index value for each scan region is the preset maximum value (recommendable for each scan region) or less, the operator can confirm that the setting of the maximum value of the index value for each scan region is within the safe range.

Additionally, the control processor 11 can display, on the display 10 via the display controller 9, that the maximum value of the index value for each scan region in the preset information is the recommendable maximum value or less for each scan region, during a desired period from the activation of the apparatus to the end of the scan. The matter relating to the display of this recommendable maximum value or less similarly applies to the embodiments which will be described below.

Additionally, the control processor 11 can display an elapsed time from the start of a scan on the display 10 via the display controller 9. At this time, since there is a recommendation of a scan time for each TI value relating to a thermal action, the recommended scan time and the elapsed time from the start of scan may be displayed side by side. The matter relating to the display of the elapsed time similarly applies to the embodiments which will be described below.

<Third Embodiment>

Next, an ultrasonic diagnostic apparatus according to a third embodiment is described with reference to FIG. 1.

The present embodiment is a modification of the first or second embodiment, and is adaptive to a case in which, although there is no need to change the maximum value of the MI value during an examination after the start of a scan, the operator sets the maximum value of the MI value for each scan region. Examples of application of this embodiment include a case in which a maximum value of a regulation value relating to an ultrasonic output, which differs from the standard stipulated by a country, is used in a medical institution, and a case in which the standard relating to ultrasonic safety in each country is a compliance item and a function of inputting the maximum value of the index value to the preset information by each operator is needless. Specifically, in the present embodiment, the maximum value of the index value is saved in system information which is higher in level than the preset information, and the preset information for each operator is edited batchwise.

In addition, in the present embodiment, the control processor 11 of the ultrasonic diagnostic apparatus 1 is configured to realize a function (f11) which prompts an input of operator identification information and an operation permission function (f12) by executing the control program.

(f11) A function which prompts the operator, who operates the adjustment function (f2) and first switching function (f3), to input operator identification information of this operator.

(f12) An operation permission function which collates the operator identification information, which was input from the input unit 13, with the operator identification information stored in the internal storage unit 12, and permits the operation of the adjustment function (f2) and first switching function (f3) when both agree.

However, the functions (f11) and (f12) are arbitrary additional matters, and may be omitted.

Figure 6:
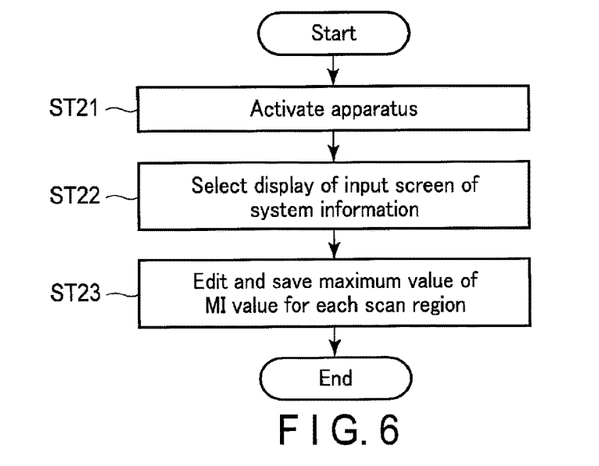
FIG. 6 is a flowchart for describing an operation of an ultrasonic diagnostic apparatus according to a third embodiment.

Next, the operation of the ultrasonic diagnostic apparatus with the above-described configuration is described with reference to a flowchart of FIG. 6.

If the ultrasonic diagnostic apparatus 1 is activated by, for example, an operation of the input unit 13 by an operator (ST21), the display of an input screen of system information is selected by a select operation of the input unit 13 by the operator (ST22).

In accordance with this selection, for the purpose of operator authentication, the control processor 11 displays, on the display 10 via the display controller 9, a message prompting the input of operator identification information of an operator who has an editing privilege. In addition, in the ultrasonic diagnostic apparatus 1, operator identification information is input from the input unit 13 or the like by the operator's operation.

The control processor 11 collates the input operator identification information with the operator identification information in the internal storage unit 12.

If both agree as a result of collation, the control processor 11 permits the operation of the ultrasonic output adjustment dial 17, MI limit button 16 and MI maximum value select dial 15, and causes the display to display the input screen of system information via the display controller 9.

In the ultrasonic diagnostic apparatus 1, while the input screen of system information is being displayed, the control processor 11 edits the system information by the operation of the input unit 13 or the like by the operator, and saves the edited system information in the internal storage unit 12. At this time, the control processor 11 edits and saves the maximum value of the MI value relating to the ultrasonic output, with respect to each scan region in the system information (ST23). In the meantime, when the system information includes the maximum value of the MI value relating to the ultrasonic output with respect to each scan region, each kind of ultrasonic probe, and each country for shipment, the maximum value is edited and saved with respect to each scan region, each kind of ultrasonic probe, and each country for shipment.

Subsequently, the ultrasonic diagnostic apparatus 1 starts scan by the operator's operation, based on the preset information of each operator.

While a scan is being executed, the ultrasonic diagnostic apparatus 1 transmits/receives ultrasonic waves to/from the patient, acquires a tomogram of the patient's scan region, based on the obtained reception signal, and displays the tomogram on the display 10.

At this time, the control processor 11 controls the ultrasonic output so as not to exceed the maximum value of the MI value in the preset information.

The above is a flow of a series of operations in the case of using the present embodiment.

In the present embodiment, the maximum value of the index value (e.g., MI value) relating to the ultrasonic output is edited and saved with respect to each scan region in the system information. By this configuration, the preset information for each operator can be edited batchwise, in addition to the advantageous effects of the first or second embodiment. This system information is higher-level setting information than the preset information. Specifically, in the present embodiment, since the information, which is given as the system information, is automatically reflected in the preset information, each operator does not need to adjust the maximum value of the index value in the preset information. Furthermore, with use of the present configuration, when the maximum values of regulation values relating to different ultrasonic outputs are to be set for respective scan regions and respective operators, arbitrary maximum values may be included in respective presets within the range of the maximum value or less of the regulation value relating to the ultrasonic output designated in the system information.

Accordingly, when a desired MI value was set in the system information as the maximum value of the index value, a transition occurs to such a state in which the maximum value of the MI value in the preset information, which was prepared at a time of shipment, was automatically changed to the desired MI value that was set in the system information. Thus, there is no need to write the maximum value of the MI value in the preset information in order to only suppress the effect of ultrasonic waves on a living body. Incidentally, although there is no particular need to change the preset information, the preset information may be changed like the first or second embodiment. All operators, or only an operator with an editing privilege, may be permitted to perform the operation of changing the maximum value of the MI value in the system information (or preset information). In the present embodiment, the case is described in which only the operator with an editing privilege is permitted.

In this case, the input operator identification information is collated with the operator identification information in the internal storage unit 12. If both agree, it is recognized that the operator has the editing privilege, and the operator is permitted to operate the ultrasonic output adjustment dial 17, MI limit button 16 and MI maximum value select dial 15. Thereby, only the operator with the editing privilege can change the maximum value of the index value of the ultrasonic output.

<Fourth Embodiment>

Next, an ultrasonic diagnostic apparatus according to a fourth embodiment is described with reference to FIG. 1.

The present embodiment is a concrete example of the first embodiment, and is adaptive to a case of setting the maximum value of the MI value for each scan region at a time of shipment of the apparatus, without giving the editing privilege of the maximum value of the MI value to the operator.

Specifically, for example, the ultrasonic diagnostic apparatus 1 is configured such that internal information, which can be written by only the apparatus maker, is prestored in the internal storage unit 12. The internal information is higher-level setting information than the system information, and includes the maximum value of the index value relating to the ultrasonic output with respect to each scan region, each kind of ultrasonic probe, and each country for shipment.

According to the above-described configuration, the apparatus maker can set the maximum value of the MI value for each scan region in the internal information at a time of apparatus shipment, without giving the editing privilege of the maximum value of the MI value to the operator.

According to at least one of the above-described embodiments, the maximum value of the index value (e.g., MI value) relating to the ultrasonic output is stored with respect to each scan region of a subject, and the ultrasonic output is controlled so as not to exceed the maximum value of the index value.

Thereby, it is possible to suppress the biological effect of ultrasonic waves to the maximum value or less of the index value for each scan region, and to maintain safety, regardless of scan modes.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultrasonic diagnostic apparatus configured to acquire a tomogram of a subject and to display the tomogram, based on a reception signal which is obtained by transmitting/receiving ultrasonic waves to/from the subject, the apparatus comprising:
   an ultrasonic probe configured to transmit/receive the ultrasonic waves to/from the subject;
   maximum value memory circuitry to store a maximum value of an index value relating to an ultrasonic output, with respect to each of scan regions of the subject;
   select circuitry configured to select a scan region of the subject based on an operation of an operator; and
   an ultrasonic output controller configured to acquire, from the maximum value memory circuitry, the maximum value of the index value corresponding to the scan region selected by the select circuitry, and control the ultrasonic output such that the ultrasonic output does not exceed the maximum value of the index value,
   a first display to display a current index value relating to the ultrasonic output;
   an adjuster configured to adjust the ultrasonic output in accordance with the operation of the operator, when the ultrasonic output controller is in an OFF state;
   first switching circuitry configured to effect switching between an ON state and an OFF state of the ultrasonic output controller by the operation of the operator;
   write circuitry configured to write, when the ultrasonic output controller is switched to the ON state by the first switching circuitry, the current index value, which is being displayed in accordance with the adjusted ultrasonic output, as the maximum value in the maximum value memory circuitry; and
   a second display to display, at a preset start time, a confirmation message that prompts confirmation of use of the maximum value stored in the maximum value memory circuitry.

2. The ultrasonic diagnostic apparatus of claim 1, wherein the maximum value memory circuitry stores the maximum value of the index value with respect to each of the scan regions and each kind of the ultrasonic probe.

3. The ultrasonic diagnostic apparatus of claim 1, wherein the maximum value memory circuitry stores the maximum value of the index value with respect to each of the scan regions and each of a plurality of countries for shipment.

4. The ultrasonic diagnostic apparatus of claim 1, wherein the ultrasonic output controller is configured to control the ultrasonic output such that the ultrasonic output does not exceed the maximum value of the index value in all scan modes.

5. The ultrasonic diagnostic apparatus of claim 1, wherein the adjuster and the first switching circuitry are configured to change the maximum value in the maximum value memory circuitry to the current index value via the write circuitry in accordance with the operation of the operator.

6. The ultrasonic diagnostic apparatus of claim 5, further comprising:
   operator identification information memory circuitry to store operator identification information of the operator who was permitted to operate the adjuster and the first switching circuitry;
   circuitry configured to prompt the operator, who operates the adjuster and the first switching circuitry, to input the operator identification information of the operator; and
   operation permission circuitry configured to collate the input operator identification information with the stored operator identification information, and to permit, when both agree, the operation of the adjuster and the first switching circuitry.

7. The ultrasonic diagnostic apparatus of claim 1, further comprising:
   comparison circuitry configured to compare the current index value displayed on the first display, and the maximum value in the maximum value memory circuitry; and
   alert circuitry configured to output an alert to the operator, when the current index value is the maximum value or more, as a result of the comparison.

8. The ultrasonic diagnostic apparatus of claim 7, further comprising:
   second switching circuitry configured to effect switching between an ON state and an OFF state of the alert circuitry by the operation of the operator.

9. The ultrasonic diagnostic apparatus of claim 1, further comprising:
   third switching circuitry configured to effect switching between an ON state and an OFF state of the second display by the operation of the operator.

10. The ultrasonic diagnostic apparatus of claim 1, further comprising:
    a third display to display whether the maximum value for each of the scan regions in the maximum value memory circuitry is a preset maximum value or less.

* * * * *